(12) United States Patent
Ding et al.

(10) Patent No.: US 9,651,489 B2
(45) Date of Patent: *May 16, 2017

(54) ASSAY DEVICE HAVING RHOMBUS-SHAPED PROJECTIONS

(75) Inventors: Zhong Ding, Pittsford, NY (US); David Bergman, Uppsala (SE)

(73) Assignee: Ortho-Clinical Diagnostics, Inc., Raritan, NJ (US)

(*) Notice: Subject to any disclaimer, the term of this patent is extended or adjusted under 35 U.S.C. 154(b) by 1383 days.

This patent is subject to a terminal disclaimer.

(21) Appl. No.: 13/438,988

(22) Filed: Apr. 4, 2012

(65) Prior Publication Data

US 2012/0258479 A1    Oct. 11, 2012

Related U.S. Application Data

(60) Provisional application No. 61/472,237, filed on Apr. 6, 2011.

(51) Int. Cl.
  *G01N 33/543*    (2006.01)
  *G01N 21/64*     (2006.01)
  (Continued)

(52) U.S. Cl.
  CPC .... *G01N 21/6428* (2013.01); *B01L 3/502746* (2013.01); *G01N 21/76* (2013.01); *G01N 21/8483* (2013.01); *G01N 33/558* (2013.01); *B01L 2200/16* (2013.01); *B01L 2300/0681* (2013.01); *B01L 2300/0816* (2013.01); *B01L 2400/0406* (2013.01); *B01L 2400/086* (2013.01)

(58) Field of Classification Search
None
See application file for complete search history.

(56) References Cited

U.S. PATENT DOCUMENTS 5,120,643 A    6/1992   Ching et al.
5,559,041 A    9/1996   Kang et al.
(Continued)

FOREIGN PATENT DOCUMENTS

WO    WO 03/103835 A1    12/2003
WO    WO 2005/089082 A2   9/2005
(Continued)

*Primary Examiner* — Chris L Chin
(74) *Attorney, Agent, or Firm* — Barclay Damon, LLP (57) ABSTRACT

An assay device includes: a liquid sample receiving zone; a capture zone in fluid communication with the sample receiving zone having capture elements bound thereto, the capture zone having a substrate and projections which extend substantially vertically from the substrate, the projections having a rhombus-shaped cross-section and the projections arranged on the substrate with the corners of the projections facing upstream in a direction toward the sample receiving zone. The projections have a height, cross-section and a distance between one another that defines a capillary space between the projections capable of generating capillary flow parallel to the substrate surface; and a sink in fluid communication with the capture zone having a capacity to receive liquid sample flowing from the capture zone. The sample receiving zone, the capture zone and the sink define a fluid flow path. Preferably, the rhombus-shaped cross-section is a square or a diamond.

21 Claims, 8 Drawing Sheets

(51) Int. Cl.
*G01N 21/76* (2006.01)
*G01N 21/84* (2006.01)
*B01L 3/00* (2006.01)
*G01N 33/558* (2006.01)

(56) References Cited

U.S. PATENT DOCUMENTS

| | | |
|---|---|---|
| 5,707,799 A | 1/1998 | Hansmann et al. |
| 5,714,389 A | 2/1998 | Charlton et al. |
| 6,156,273 A | 12/2000 | Regnier et al. |
| 6,228,660 B1 | 5/2001 | May et al. |
| 6,254,754 B1 | 7/2001 | Ross et al. |
| 6,372,542 B1 | 4/2002 | Martin et al. |
| 6,733,682 B1 | 5/2004 | Bjorkman et al. |
| 6,811,736 B1 | 11/2004 | Ohman et al. |
| 6,884,370 B2 | 4/2005 | Ohman et al. |
| 7,416,700 B2 | 8/2008 | Buechler et al. |
| 8,974,749 B2 * | 3/2015 | Bergman ............. G01N 33/558 422/502 |
| 2005/0042766 A1 | 2/2005 | Ohman et al. |
| 2006/0239859 A1 | 10/2006 | Ohman et al. |
| 2007/0231883 A1 | 10/2007 | Lindstrom et al. |

FOREIGN PATENT DOCUMENTS

| | | |
|---|---|---|
| WO | WO 2005/118139 A1 | 12/2005 |
| WO | WO 2006/137785 A1 | 12/2006 |
| WO | WO 2007/149042 A1 | 12/2007 |

* cited by examiner

FIG. 6A
Level 1 (2 pg/ml)

FIG. 6B
Level 2 (59 pg/ml)

ASSAY DEVICE HAVING RHOMBUS-SHAPED PROJECTIONS

CROSS REFERENCE TO RELATED APPLICATION

This patent application is a Non-Provisional of U.S. Provisional Application No. 61/472,237, filed Apr. 6, 2011, the disclosure of which is incorporated by reference in its entirety.

FIELD OF THE INVENTION

The present invention relates to the field of diagnostic assays, and in particular to lateral flow assays where an analyte to be detected is present in a biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, and skin or throat swabs. These assays are frequently expected to give a fast and reliable result, while being easy to use and cheap to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a capture zone, and optionally a transport or incubation zone connecting the receiving and capture zone, respectively. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-receiving zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Figure 1:
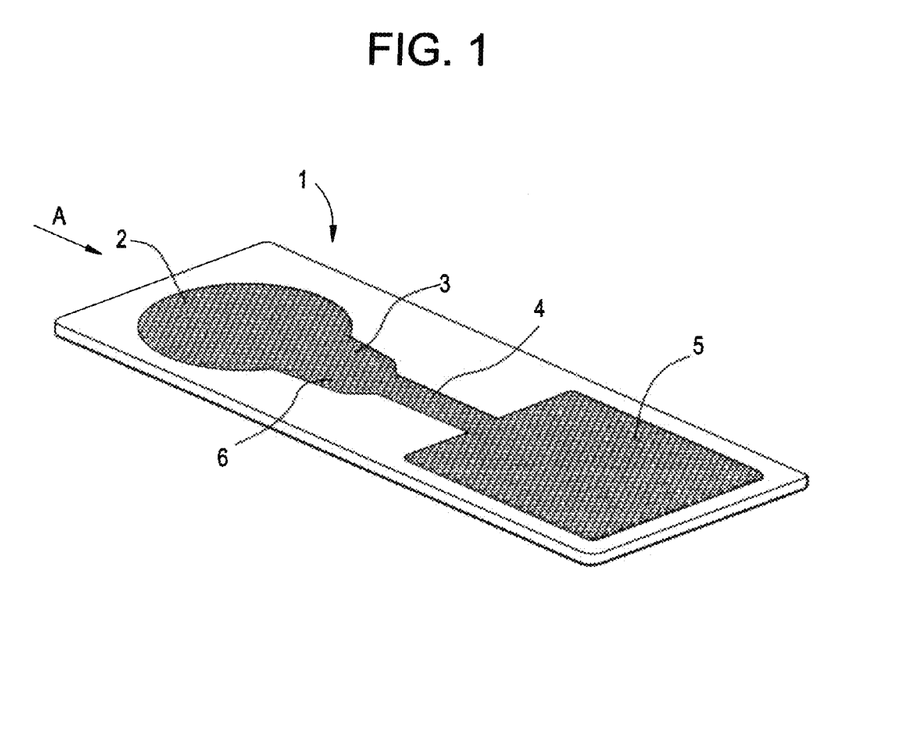
FIG. 1 shows an assay device according to a preferred embodiment of the present invention.

Another type of assay devices is a non-porous assay having projections to induce capillary flow. A non-porous assay device is shown in FIG. 1. Examples of such assay devices include the open lateral flow device as disclosed in WO 03/103835, WO 2005/089082, WO 2005/118139, and WO 2006/137785, all of which are incorporated herein by reference in their entireties.

U.S. Pat. No. 6,156,273 discloses separation columns that include collocated monolith support structures and interconnected channels defined by the support structures.

In known assay devices having projections with round cross-sections, there are several problems associated with such round-cross sections. One drawback is the relatively large stagnation area in the front and the back of the projection, which is believed to contribute to spikes in signal due to trapped analyte conjugated with label and poor washing. Another drawback is the relatively large background signal generated by the geometry of the round projection. Yet another drawback is the thick depletion layer with a symmetric round pillar arrangement, which slows the capture of the labeled analyte, leading to decreased sensitivity.

Accordingly, there is a need for further improved kinetics, increased sensitivity and specificity in methods and devices for biochemical and biomolecular assays, in particular for diagnostic assays where the requirements for sensitivity and accuracy are very high. In particular, there is a need for a projection geometry that can minimize background signal with a thin depletion layer and minimized stagnation regions surrounding the projections.

SUMMARY OF THE INVENTION

The present invention is directed to a method that alleviates one or more the foregoing problems described above.

One aspect of the invention is directed to an assay device, which includes: a liquid sample receiving zone; a capture zone in fluid communication with the sample receiving zone having capture elements bound thereto, the capture zone having a substrate and projections which extend substantially vertically from the substrate, the projections having a rhombus-shaped cross-section and the projections arranged on the substrate with the corners of the projections facing upstream in a direction toward the sample receiving zone, wherein the projections have a height, cross-section and a distance between one another that defines a capillary space between the projections capable of generating capillary flow parallel to the substrate surface; and a sink in fluid communication with the capture zone having a capacity to receive liquid sample flowing from the capture zone, wherein the sample receiving zone, the capture zone and the sink define a fluid flow path. In a preferred embodiment the rhombus-shaped cross-section is a square. In another preferred embodiment the rhombus-shaped cross-section is a diamond. In yet another preferred embodiment, the corners of the projections facing the upstream and downstream direction have a smaller interior angle compared to the other interior angles of the projections.

According to another aspect of the invention, there has been provided a method for performing an assay on a liquid sample for the detection of one or more analytes of interest. The method includes: providing a liquid sample receiving zone for receiving the liquid sample; providing a capture zone in fluid communication with the sample receiving zone having capture elements bound thereto, the capture zone having a substrate and projections which extend substantially vertically from the substrate, the projections having a rhombus-shaped cross-section and the projections arranged on the substrate with the corners of the projections facing upstream in a direction toward the sample receiving zone, wherein the projections have a height, cross-section and a distance between one another that defines a capillary space between the projections capable of generating capillary flow parallel to the substrate surface; providing a sink in fluid communication with the capture zone having a capacity to receive liquid sample flowing from the reaction zone; dispensing the sample onto the sample receiving zone, whereby the sample flows by capillary action along through the capture zone and into the sink; and reading a signal to determine the presence or concentration of the one or more analyte.

Further objects, features and advantages of the present invention will be apparent to those skilled in the art from detailed consideration of the preferred embodiments that follow.

DETAILED DESCRIPTION OF PREFERRED EMBODIMENTS

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" here means a volume of a liquid, solution or suspension, intended to be subjected to qualitative or quantitative determination of any of its properties, such as the presence or absence of a component, the concentration of a component, etc. Typical samples in the context of the present invention are bodily fluids such as blood, plasma, serum, lymph, urine, saliva, semen, amniotic fluid, gastric fluid, phlegm, sputum, mucus, tears, stool, etc. The embodiments of the present invention are applicable to all bodily samples, but preferably to samples of whole blood.

In the present invention, the determination based on lateral flow of a sample and the interaction of components present in the sample with reagents present in the device and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesitas, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids and complexes and derivatives thereof.

The terms "zone", "area" and "site" are used in the context of this description, examples and claims to define parts of the fluid passage on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

The present invention is directed to a lateral flow assay device for determining the presence or amount of at least one analyte. FIG. 1 shows a preferred embodiment of such a device according to the invention. The assay device 1, has at least one sample addition zone 2, optionally at least one detection element zone 3 (also commonly referred to as a "conjugate zone"), at least one capture zone 4 optionally comprising several capture zones (not shown), placed in parallel between the sample receiving zone and at least one sink 5. The zones form a flow path by which sample flows from the sample addition zone to the sink. Also included are capture elements in the capture zone 4, capable of binding to the analyte, optionally deposited on the device (such as by coating); and a detection element also capable of binding to the analyte, optionally deposited on the device in the detection zone, wherein the detection element carries a first label for detection in the capture zone.

Components of the assay device (i.e., a physical structure of the device whether or not a discrete piece from other parts of the device) can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being milled or injection molded or from surfaces of copper, silver and gold films upon which are adsorbed various long chain alkanethiols. The structures of plastic which are capable of being milled or injection molded can comprises a polystyrene, a polycarbonate, or a polyacrylate. In a particularly preferred embodiment, the assay device is injection molded from a cyclo olefin polymer, such as those sold under the name Zeonar®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, capillaries. Preferably the flow path comprises a lateral flow path of adjacent projections, having a size, shape and mutual spacing such that capillary flow is sustained through the flow path. In at least the capture zone the flow path will include those rhombus-shaped projections according to the present invention. In one embodiment, the flow path is in a channel within the substrate having a bottom surface and side walls. In this embodiment, the projections protrude from the bottom surface of the channel. The side walls may of may not contribute to the capillary action of the liquid. If the sidewalls do not contribute to the capillary action of the liquid, then a gap can be provided between the outermost projections and the sidewalls to keep the liquid contained in the flow path defined by the projections.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 20 to about 80 µm, and a distance or distances between the projections of about 3 to about 200 µm, preferably 10 to about 100 µm or 10 to 50 µm from each other. The flow channel may have a length of about 5 to about 500 mm, preferably about 10 to about 100 mm, and a width of about 1 to about 30 mm, preferably about 2 to about 10 mm.

The liquid sample receiving zone 2 receives sample from a sample dispenser, such as a pipette. The sample is typically deposited onto the top of the zone. The sample receiving zone is capable of transporting the liquid sample from the point where the sample is deposited to the capture zone, preferably through capillary flow. The capillary flow inducing structure can include porous materials, such as nitrocellulose, or preferably through projections, such as micropillars, as shown in FIG. 1.

A filter material can be placed in the sample receiving zone to filter particulates from the sample or to filter blood cells from blood so that plasma can travel further through the device.

Downstream from the liquid sample receiving zone is the capture zone 4 which is in fluid communication with the sample receiving zone. The capture zone 4 includes projections having the rhombus-shaped cross-sections according to the present invention. As noted above, these projections are preferably integrally molded into the substrate from an optical plastic material such as Zeonar.

The present invention is based, in part, on the surprising discovery that an assay device such as those described herein having projections in the capture zone having a rhombus-shaped cross-sections provides greater sensitivity, better precision, and reduced background noise. While not wishing to be bound by any theory, applicants believe that the use of projections having a round cross section results poorer flow of the sample fluid around the pillars. In particular, flow of a fluid through a zone having round cross-section projections results in a relatively large stagnation area in the front and back of the projection, which in turn leads to a poor washing of unbound detection elements. This can result in labeled antigen or the label itself being trapped in the front and back of the pillar, which results in an increased background signal and decreased sensitivity.

Figure 2:
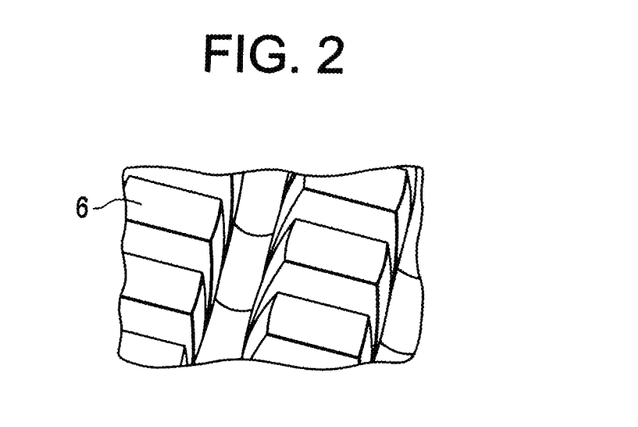
FIG. 2 shows a square-shaped projection of a lateral flow assay device according to a preferred aspect of the invention.
Figure 3A:
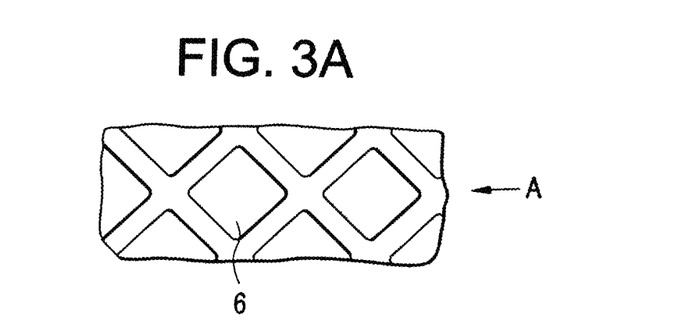
FIG. 3A shows a top view of the projection depicted in FIG. 2.
Figure 3B:
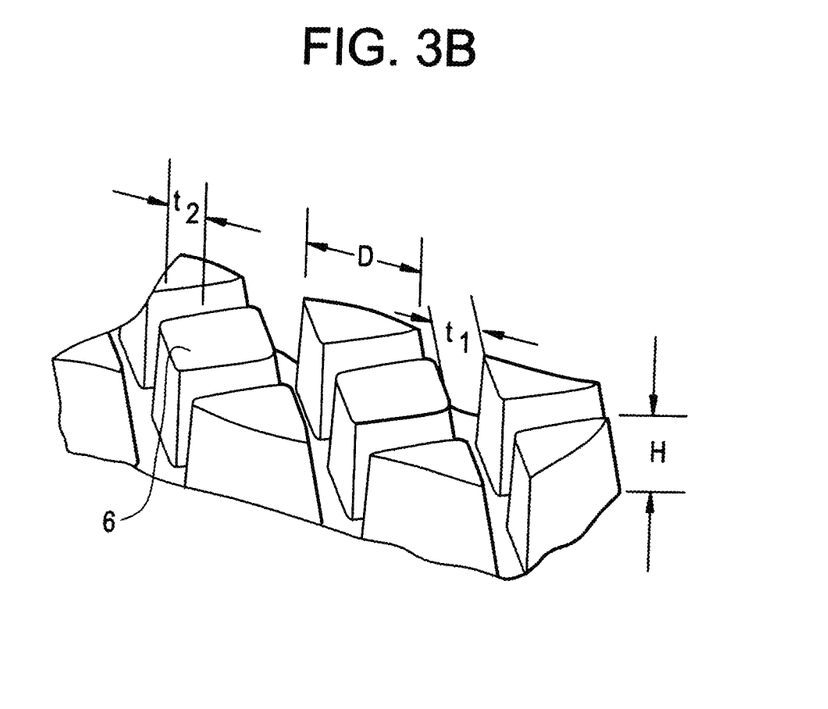
FIG. 3B shows a perspective view of the projection shown in FIG. 2.

The inventors also found that a projection having any rectangular cross-section would not improve upon the round-cross section design. Instead, it was found that only a rhombus-shaped cross-section would provide a greater sensitivity and reduced background noise relative to a projection having a round cross-section. As is known, a rhombus is a quadrilateral having four sides whose four sides have the same length, such as a diamond, or if the rhombus has right angles, a square. Rhombus-shaped pillars are shown in FIGS. 1-3. FIGS. 3A and 3B are the top and the perspective view of the rhombus-shaped projections.

The size of the rhombus-shaped projections can vary widely and are selected in part to induce capillary flow in the fluid passing through the capture zone and can include the dimensions described above for projections in general. In a preferred embodiment, the projection height is about 65 µm with the sides of the pillars about 50 µm on the bottom and 40 µm on top. The distance between pillars is about 10 µm in bottom and 20 µm on top. The corner of the rhomus-shaped projection always faces the fluid flow direction to minimize the stagnation. Fluid flow relative to the projections is shown as arrow A in FIGS. 1 and 3A.

The rhombus-shaped projections according to the present invention as shown in FIGS. 2, 3A and 3B have much a smaller stagnation area in the front and the back of the projection as compared with the round one. The surface area/volume ratio also increased as compared to the projection having a round cross-section.

The projections having a rhombus-shaped cross-section are included in the capture zone of the assay of the present invention described in more detail below.

Attached to the projections in the capture zone are capture elements. The capture elements can include molecules suitably chosen for their affinity to the marker or analyte of interest or their affinity to relevant modifications of the marker or analyte. For example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable modification of a capture element is a biotin substituted target biological compound, in which case the probe may bear avidin functionality. The capture zone can include multiple capture zones. The multiple capture zones can be used for assays that include one or more markers. In the event of multiple capture zones, the capture elements can include multiple capture elements, such as first and second capture elements.

Downstream from the capture zone is a sink in fluid communication with the capture zone. The sink is an area of the assay device with the capacity of receiving liquid sample. The sink provides a capillary force to continue moving the liquid sample through and out of the capture zone. The sink can include a porous material such as nitrocellulose or can be a non-porous structure such as the projections described herein. The sink can also include non-capillary fluid driving means, such as using evaporative heating or a pump. Further details of sinks as used in assay devices according to the present invention can be found in patent publications US 2005/0042766 and US 2006/0239859, both of which are incorporated herein by reference in their entireties.

Optionally located between the sample addition zone and the capture zone is a detection element zone. This zone includes a detection element which attaches to the analyte as the analyte flows through the detection element zone. The detection element is subsequently detected in the capture zone as described in more detail below. The detection elements can be attached directly to the marker or analyte, or more commonly may be conjugated to a detection capture element which then binds to the analyte. Hence, the term "detection element" is meant to encompass a detectable moiety that can be attached directly to the marker or analyte or conjugated to a detection capture element. Suitable detection capture elements can include those described above with respect to the capture elements.

In the case of a competitive assay, the detection element zone will contain analyte having detection element already bound to the analyte. In this instance, as the sample moves through the detection element zone, the previously deposited analyte having the detection element bound thereto will be transported along with analyte in the sample to the capture zone.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element is preferably a label chosen from chromophores, fluorophores, radioactive labels, and enzymes. Suitable labels are available from commercial suppliers, providing a wide range of dyes for the labeling of antibodies, proteins, and nucleic acids. There are for example fluorophores spanning practically the entire visible and infrared spectrum. Suitable fluorescent or phosphorescent labels include for instance, but are not limited to, fluoresceins, Cy3, Cy5 and the like. Suitable chemiluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}$I and $^{32}$P.

Suitable enzymatic labels are for instance but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

In one embodiment, the detection element is pre-deposited on the assay device, and the capture element is added after or together with the addition of the sample. Alternatively, the capture element is pre-deposited on the assay device, and the detection element is added after or simultaneously with the addition of the sample. Preferably, both the detection and capture elements are pre-deposited on the assay device, on the detection zone and capture zone, respectively.

In one embodiment, the detection and capture elements are transported by the sample, through the influence of capillary force, to the capture zone, forming a detection complex, which includes the detection element, the marker and the capture element.

Preferably the entirety of the flow path including the sample receiving zone, the capture zone and the sink includes projections substantially vertical in relation to the substrate, and having a height, diameter and reciprocal spacing capable of creating lateral flow of the sample in the flow path. This preferred embodiment is shown in FIG. 1.

In any of the above embodiments, the device is preferably a disposable assay device. The assay device is preferably contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample receiving zone of the assay device, such as through a port in the housing of the device. The sample moves by capillary action through an optional filter and into the detection element zone where it is conjugated with a detection element, either directly or indirectly, such as through an antibody. In an alternative embodiment, the detection element may be added to the device together with the sample, such that no detection element zone is necessary. Next the sample moves by capillary action into the capture zone, where it encounters the projections having the rhombus-shaped cross-section. The analyte(s) of interest, having the detection element, is captured in the capture zone, such as by antibodies on the surface of the capture zone. The reader as described above is then used to read the signal that is generated by the detection element to determine the presence or concentration of the analyte(s). The sample moves from the capture zone and into the sink. The reader may read the signal immediately or a short time after the sample has moved through the capture zone. Also, one or more washes may follow the sample through the device to wash any unbound detection element away from the capture zone.

The method, assay device, and reader according to an embodiment of the invention have many advantages, mainly related to the improved reaction kinetics of the immunochemical reactions and the increased sensitivity of the assay.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Figure 6A:
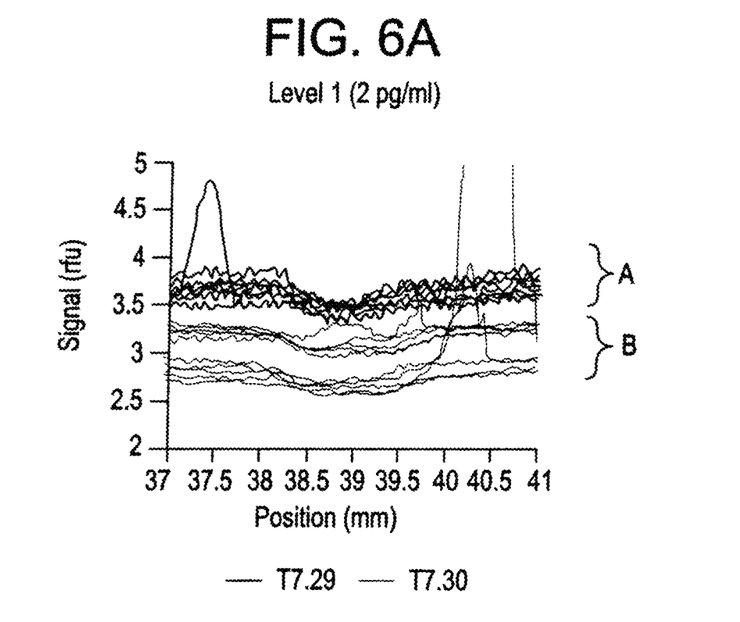
FIGS. 6A and B show the background noise for a round and square projection.
Figure 6B:
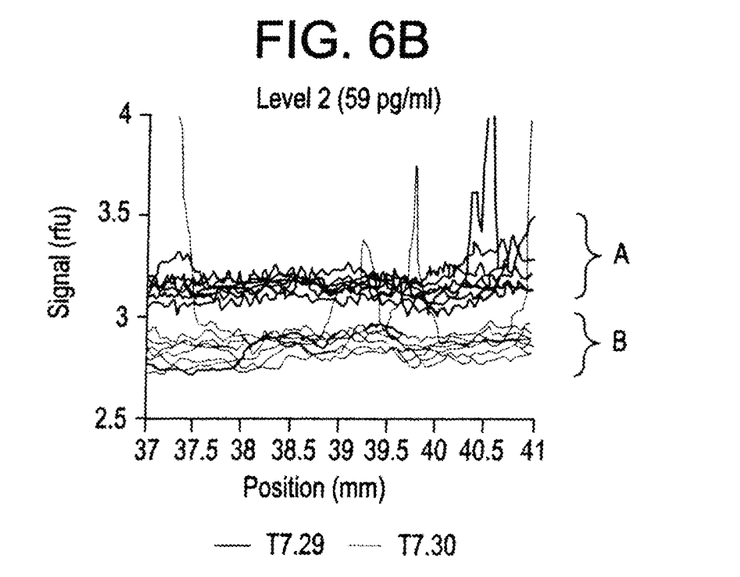

Plastic substrate chips made of Zeonor (Zeon, Japan) having oxidized dextran on the surface for covalently immobilization of proteins via Shiffs base coupling were used. A capture zone in the flow channel was deposited (Biodot AD3200) with anti-NT-proBNP mAb (15C4 Hytest) and dried. A detection element zone in the flow channel was deposited with anti-NT-proBNP mab (S-1.21.3 Roche) and dried. A small amount of Triton X-45 was deposited on the device to increase wettability of the sample for better capillary flow. Sample was added to the sample zone of the device and the capillary action of the micropillar array distributed the sample across the detection element zone, the capture zone and into the wicking zone. A typical assay time was about 10 minutes. The signal intensities were recorded in a prototype line-illuminating fluorescence scanner. The results from the experiments are shown in FIGS. 4, 6 and Table 1.

Figure 4:
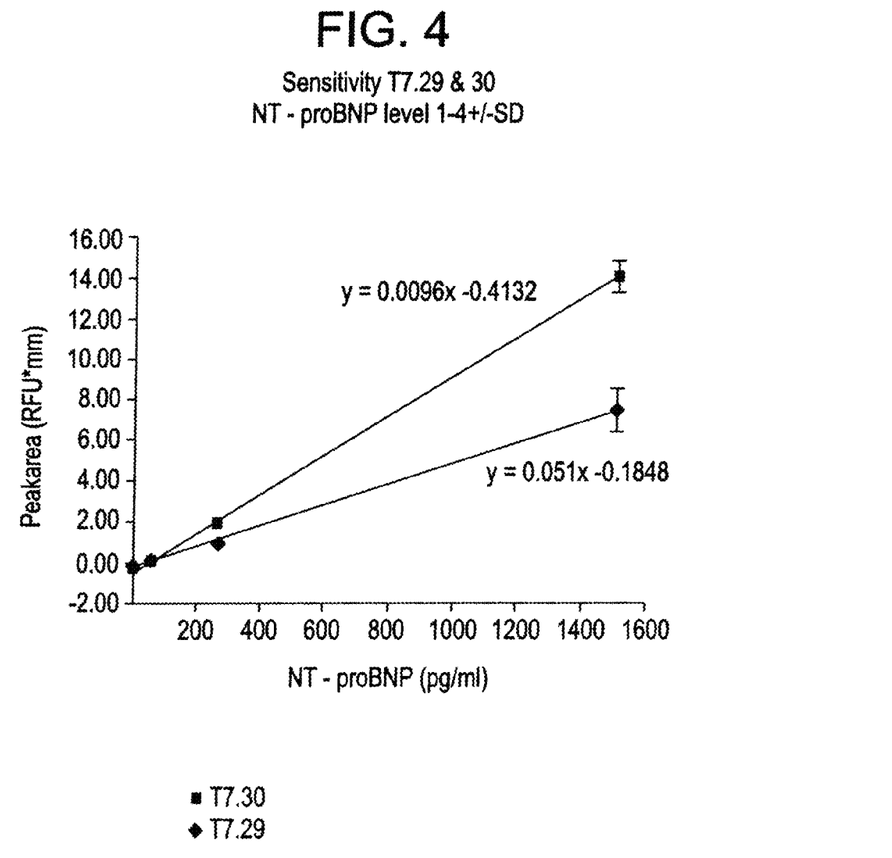
FIG. 4 shows a graph of sensitivity vs. NT-proBNP concentration for a square-shaped projection and a round shaped.

FIG. 4 shows the experimental results with the projections having a square-shaped cross-section designated as T7.30 (shown in squares (■)) and projections having a round cross-section T7.29 (shown in diamonds (♦). As the graph shows, square-shaped projections have a much higher optical signal, indicating a higher analyte capture as compared to the round-shaped projection. In fact, as the graph shows at a NT-proBNP level of 1450 pg/ml the signal is approximately twice as strong for the square-shaped projection as the round projection (14 vs. 7, respectively).

Table 1 below demonstrates the improvement in assay precision using square projections vs. round projections. Specifically, the coefficient of variation (CV), which is a measure of precision, is significantly smaller at levels 3 (268 pg/ml) and 4 (1499 pg/ml) for a square projection indicating higher precision. For the lower levels (1 and 2) no effect on CV was seen between the square and round projections.

TABLE 1

|  |  | T7.29 | | T7.30 | |
| --- | --- | --- | --- | --- | --- |
|  |  | Area | Height | Area | Height |
| Level 1 | Average | −0.03 | 0.12 | −0.21 | 0.04 |
| 2 pg/ml | SD | 0.06 | 0.02 | 0.04 | 0.02 |
|  | CV (%) | 183 | 14 | 21 | 60 |
|  | N | 10 | 10 | 8 | 8 |
| Level 2 | Average | 0.14 | 0.14 | 0.13 | 0.13 |
| 59 pg/ml | SD | 0.05 | 0.03 | 0.09 | 0.06 |
|  | CV (%) | 40 | 19 | 76 | 44 |
|  | N | 10 | 10 | 9 | 9 |
| Level 3 | Average | 0.98 | 0.97 | 1.95 | 1.54 |
| 268 pg/ml | SD | 0.11 | 0.12 | 0.20 | 0.10 |
|  | CV (%) | 11 | 12 | 10 | 6 |
|  | N | 10 | 10 | 10 | 10 |
| Level 4 | Average | 7.46 | 7.68 | 14.05 | 12.18 |
| 1499 pg/ml | SD | 0.75 | 0.73 | 0.62 | 0.55 |
|  | CV (%) | 10 | 9 | 4 | 5 |
|  | N | 10 | 10 | 9 | 9 |

Figure 5:
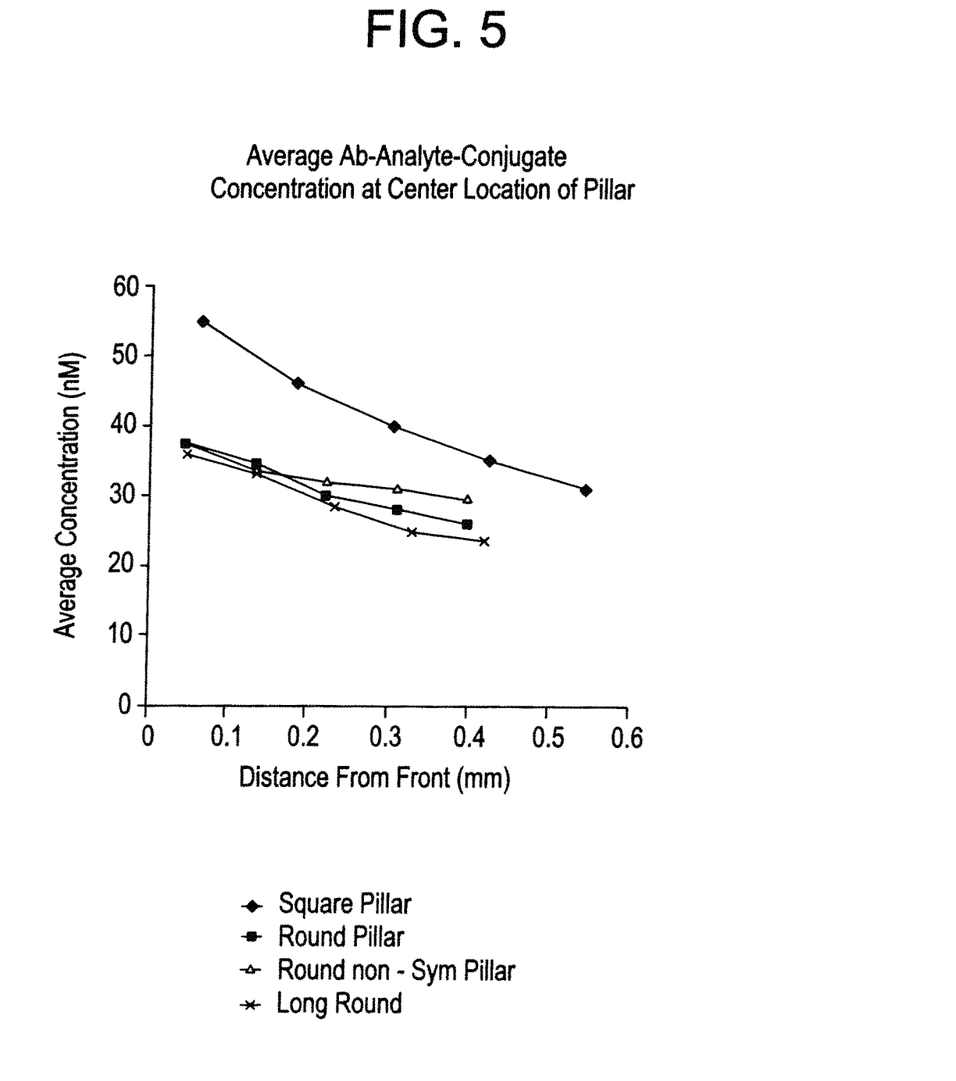
FIG. 5 shows analyte concentrations of different shaped projections and arrangement along the length of the flow path.

FIG. 5 is the computational fluid dynamics (CFD) simulation on analyte capture at the same fluid flow and the same initial analyte concentration with different cross-section projections. The CFD simulation takes into account fluid flow, diffusion, and kinetic reactions on the solid surface of the projections. The analyte concentration is a function of projection location, projection shape (square or round) and projection arrangement (symmetric or non-symmetric). The y-axis shows the average concentration of analyte at the center of the projection along the axis of symmetry. The x-axis shows the distance each pillar is from the beginning of the capture zone (i.e., where the capture antibody is first deposited onto the substrate). Each projection (termed "pillar" in the figure) is designated by a data point (e.g., a square (■)) for each of the different shaped projections. The first five projections from the beginning of the capture zone are shown. The square-shaped projections shown by diamonds (♦) had slightly larger distances between the projections, due to natural packing distance variation between the square and round projections. As the graphs show, the square-shaped projection showed a significantly higher analyte capture at all locations in the capture zone (i.e., upstream and downstream) compared with various round projection designs tested in this simulation. The results of the CFD simulation agree with experimental observations. The other shapes shown are a long round projection (X), a round projection (■) and a round non-symmetrical projection (♦).

For lower concentrations (2 and 59 pg/ml as listed in Table 1 in comparison to a higher concentration of 268 and 1499 pg/ml), the square-shaped projection also has a lower and smoother baseline as shown in FIG. 6. It indicates that the square-shaped projection also reduces the optical noise. Again, this is believed to be due to the more uniform pillar cross sectional area as compared with the round projections and a smaller stagnation area in the front and back of the projections.

Example 2

Dose response curves where evaluated using assay devices having chips with projections having round cross-sections and devices having projections with square-shaped cross-sections for intact parathyroid hormone (iPTH). Plastic substrate chips made of Zeonor (Zeon, Japan) having oxidized dextran on the surface for covalently immobilization of proteins via Schiff base coupling were used. Fluorescently labeled Goat polyclonal antibody (N-terminal, aa 1-34) Anti-iPTH was deposited and dried to create a reagent zone. Goat polyclonal antibody (C-terminal, aa 39-84) Anti-iPTH was deposited and dried to create a detection zone. A small amount of Triton X-45 was deposited on the device to increase wettability of the sample for better capillary flow. Sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. The results are shown in FIGS. 7 and 8.

Figure 7:
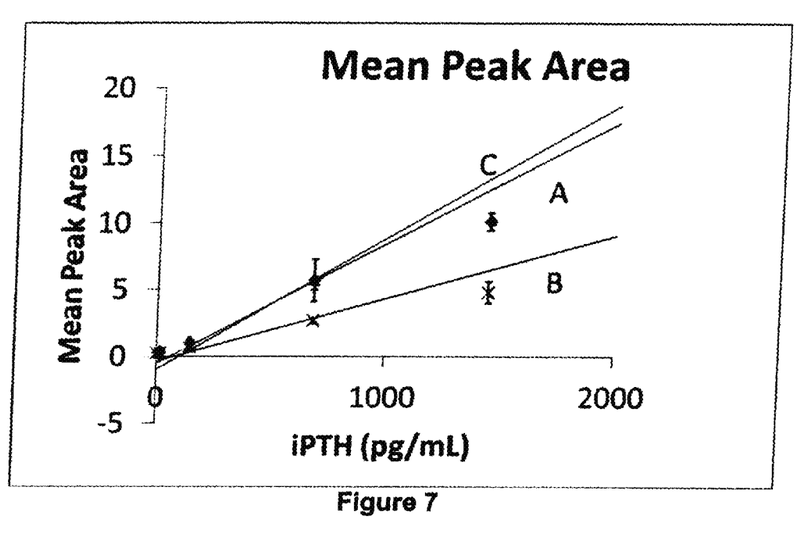
FIG. 7 shows dose response curves having mean peak areas along the y-axis and the concentration of iPTH in pg/ml along the x-axis.

FIG. 7 shows dose response curves having mean peak areas along the y-axis and the concentration of iPTH in pg/ml along the x-axis. Curve A marked with diamonds (♦) has square-shaped projections. Curve C marked with a plus sign (+) used chips identical to the curve A chips, but were deposited in a separate deposition event. Many of the data points of Curve A and C overlap. Curve B marked with an (X) is for a chip identical to chip A except that it has round projections instead of square projections. As the results shown, the mean peak area of the devices having projections with square-shaped cross-sections is significantly higher than the devices having projections with round cross-sections.

Figure 8:
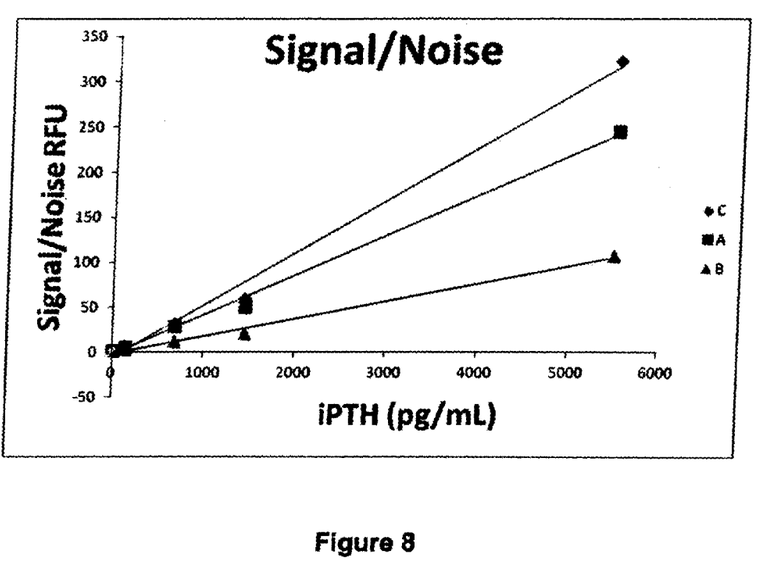
FIG. 8 shows dose response curves having mean peak areas along the y-axis and the concentration of iPTH in pg/ml along the x-axis.

FIG. 8 is similar to FIG. 7 except that lower amounts of iPTH were used. Again as in FIG. 7, FIG. 8 shows dose response curve having mean peak area along the y-axis and the concentration of iPTH in pg/ml along the x-axis. The curve marked with square (■) (A) has projections with square-shaped cross-sections. The curve marked with a diamonds (♦) (C) used devices that were identical to T7.30 that were deposited in the same manner on the same chip type in a separate deposition event. The curve marked with a triangle (▲) (B) is for a device identical to the T7.30 chip except that it has round projections instead of square projections. As the results shown, the mean peak area of the devices having square projections is significantly higher than the devices having round projections.

A small alteration of the square-shaped projection design should also maintain the advantages of the square-shaped projection in terms of smaller stagnation areas in front and back of the projections. These designs include the corners of the projections facing the upstream and downstream direction having a smaller interior angle compared to the other interior angles of the projections, i.e., a diamond-shaped projection with a the longer axis along the bulk flow direction. The front and the end of the diamond-shaped projection can be made rather sharp to further reduce the stagnation area.

Additional Embodiments

1. An assay device comprising: a liquid sample receiving zone; a capture zone in fluid communication with the sample receiving zone having capture elements bound thereto, the capture zone having a substrate and projections which extend substantially vertically from the substrate, the projections having a rhombus-shaped cross-section and the projections arranged on the substrate with the corners of the projections facing upstream in a direction toward the sample receiving zone, wherein the projections have a height, cross-section and a distance between one another that defines a capillary space between the projections capable of generating capillary flow parallel to the substrate surface; and a sink in fluid communication with the capture zone having a capacity to receive liquid sample flowing from the capture zone, wherein the sample receiving zone, the capture zone and the sink define a fluid flow path.

2. An assay device as disclosed in embodiment 1, wherein the rhombus-shaped cross section is a square.

3. An assay device as disclosed in embodiment 1, wherein the rhombus-shaped cross section is a diamond.

4. An assay device as disclosed in embodiment 3, wherein the corners of the projections facing the upstream and downstream direction have a smaller interior angle compared to the other interior angles of the projections.

5. An assay device as disclosed in embodiment 1, wherein the substrate comprises a channel having a bottom surface and side walls, and wherein the projections protrude from the bottom surface of the channel, and wherein the side walls do not contribute to the capillary action of the liquid.

6. An assay device as disclosed in embodiment 1, wherein the capillary space between the projections forces the liquid to move laterally away from where the liquid sample was applied without requiring a cover, side walls or externally applied drive means to either induce or assist the capillary flow along the flow path.

7. An assay device as disclosed in embodiment 1, further comprising a detection element zone between the capture zone and sample receiving zone, wherein the detection element zone has a detection element thereon.

8. An assay device as disclosed in embodiment 1, wherein the capture zone further comprises a plurality of captures zones, wherein a first capture element is applied to a first capture zone and a second capture element is applied to a second capture zone.

9. An assay device as disclosed in embodiment 8, wherein the first and second capture zones are separated from each other by an area having no capture elements, or the first and second capture zones are directly adjacent to one another.

10. An assay device as disclosed in embodiment 1, wherein the capture elements extend the entire width of the capture zone in a direction perpendicular to the fluid flow path.

11. An assay device as disclosed in embodiment 1, wherein the capture elements are capture antibodies.

12. An assay device as disclosed in embodiment 1, further comprising a housing for holding the sample receiving zone, capture zone and sink, the housing having a sample port located thereon in fluid communication with the sample receiving zone.

13. An assay device as disclosed in embodiment 12, further comprising a filter disposed between the sample port and the sample receiving zone.

14. An assay device as disclosed in embodiment 13, wherein the filter is capable of filtering red blood cells from plasma.

15. An assay device as disclosed in embodiment 7, wherein the detection element comprises an antibody having a detectable label bound thereto.

16. A method for performing an assay on a liquid sample for the detection of one or more analytes of interest, the method comprising the steps of: providing a liquid sample receiving zone for receiving the liquid sample; providing a capture zone in fluid communication with the sample receiving zone having capture elements bound thereto, the capture zone having a substrate and projections which extend substantially vertically from the substrate, the projections having a rhombus-shaped cross-section and the projections arranged on the substrate with the corners of the projections facing upstream in a direction toward the sample receiving zone, wherein the projections have a height, cross-section and a distance between one another that defines a capillary space between the projections capable of generating capillary flow parallel to the substrate surface; providing a sink in fluid communication with the capture zone having a capacity to receive liquid sample flowing from the reaction zone; dispensing the sample onto the sample receiving zone, whereby the sample flows by capillary action along through the capture zone and into the sink; and reading a signal to determine the presence or concentration of the one or more analyte.

17. A method as disclosed in embodiment 16, wherein the substrate comprises a channel having a bottom surface and side walls, and wherein the projections protrude from the bottom surface of the channel, and wherein the side walls do not contribute to the capillary action of the liquid.

18. A method as disclosed in embodiment 16, further comprising a detection element zone having a detection element bound thereto, wherein the analyte binds with the detection element in the detection element zone and is captured by the capture zone to produce a detectable signal.

19. A method as disclosed in embodiment 16, further comprising adding a detection element with the sample, whereby the detection element is captured in the capture zone and produces a detectable signal.

20. A method as disclosed in embodiment 16, wherein the rhombus-shaped cross section is a square.

21. A method as disclosed in embodiment 16, wherein the rhombus-shaped cross section is a diamond.

22. A method as disclosed in embodiment 16, wherein the corners of the projections facing the upstream and downstream direction have a smaller interior angle compared to the other interior angles of the projections.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

What is claimed is:

1. An assay device comprising:
   a substrate having a top surface and side walls;
   a liquid sample receiving zone;
   a detection element zone in fluid communication with the liquid sample receiving zone, the detection element zone having a detection element;
   a capture zone in fluid communication with the liquid sample receiving zone and detection element zone, the capture zone having capture elements bound thereto, each of the liquid sample receiving zone, the detection element zone and the capture zone having projections which extend substantially vertically from the top surface of the substrate, the projections in the capture zone having a rhombus-shaped cross-section wherein the projections in the capture zone are arranged on the substrate with the corners of the projections facing upstream in a direction toward the liquid sample receiving zone, wherein the projections in each of the zones have a height, cross-section and a distance between one another that defines a capillary space between the projections capable of generating capillary flow parallel to the top surface of the substrate; and
   a sink in fluid communication with the capture zone having a capacity to receive liquid sample flowing from the capture zone, wherein the liquid sample receiving zone, the detection element zone, the capture zone and the sink define a fluid flow path formed on the substrate, and in which the sink has the projections for maintaining capillary flow along the entire defined path.

2. An assay device as claimed in claim 1, wherein the rhombus-shaped cross-section is a square.

3. An assay device as claimed in claim 1, wherein the rhombus-shaped cross-section is a diamond.

4. An assay device as claimed in claim 3, wherein the corners of the projections facing the upstream and downstream direction have a smaller interior angle compared to the other interior angles of the projections.

5. An assay device as claimed in claim 1, wherein the capture zone further comprises a plurality of capture zones, wherein a first capture element is applied to a first capture zone and a second capture element is applied to a second capture zone.

6. An assay device as claimed in claim 5, wherein the first and second capture zones are separated from each other by an area having no capture elements, or the first and second capture zones are directly adjacent to one another.

7. An assay device as claimed in claim 1, wherein the capture elements extend the entire width of the capture zone in a direction perpendicular to the fluid flow path.

8. An assay device as claimed in claim 1, wherein the capture elements are capture antibodies.

9. An assay device as claimed in claim 1, further comprising a housing for holding the sample receiving zone, the detection element zone, the capture zone and sink, the housing having a sample port located thereon in fluid communication with the sample receiving zone.

10. An assay device as claimed in claim 9, further comprising a filter disposed between the sample port and the sample receiving zone.

11. An assay device as claimed in claim 10, wherein the filter is capable of filtering red blood cells from plasma.

12. An assay device as claimed in claim 1, wherein the detection element comprises an antibody having a detectable label thereto.

13. An assay device as claimed in claim 1, wherein the projections are further defined by a tapering configuration.

14. An assay device as claimed in claim 13, in which the tapered configuration of the projections includes a smaller width at the top of the projection relative to the bottom.

15. A method for performing an assay on a liquid sample for the detection of one or more analytes of interest, the method comprising the steps of:
   providing a liquid sample receiving zone on a substrate for receiving the liquid sample;
   providing a detection element zone on the substrate and in fluid communication with the liquid sample receiving zone, the detection element zone having at least one detection element carrying a first label for binding with the one or more analytes of the liquid sample;
   providing a capture zone on the substrate in fluid communication with the liquid sample receiving zone and detection element zone, the capture zone having capture elements, which bind the one or more analytes, bound thereto, each of the zones having projections which extend substantially vertically from the substrate, the projections of the capture zone having a rhombus-shaped cross-section wherein the projections in the capture zone are arranged on the substrate with the corners of the projections facing upstream in a direction toward the liquid sample receiving zone, wherein the projections in each of the zones have a height, cross-section and a distance between one another that defines a capillary space between the projections capable of generating capillary flow parallel to the substrate surface;

providing a sink on the substrate and in fluid communication with the capture zone having a capacity to receive liquid sample flowing from the capture zone, the sink having the projections provided in each of the zones;

dispensing the sample onto the liquid sample receiving zone, whereby the sample flows by capillary action along through the detection element zone to the capture zone and into the sink along a fluid flow path defined by the projections, wherein the one or more analytes having a detection element bound thereto is captured in the capture zone and produces a detectable signal; and reading the detectable signal to determine the presence or concentration of the one or more analyte.

16. A method as claimed in claim 15, wherein the analyte binds with the detection element in the detection element zone and is captured by the capture zone to produce a detectable signal.

17. A method as claimed in claim 15, wherein the rhombus-shaped cross section is a square.

18. A method as claimed in claim 15, wherein the rhombus-shaped cross section is a diamond.

19. A method as claimed in claim 15, wherein the corners of the projections facing the upstream and downstream direction have a smaller interior angle compared to the other interior angles of the projections.

20. A method as claimed in claim 15, including forming at least some of the projections with a tapered configuration.

21. A method as claimed in claim 20, in which the tapered configuration is formed with each projection having a smaller width at the top of the projection relative to the bottom.

* * * * *